United States Patent [19]

Xu et al.

[11] Patent Number: 6,066,487
[45] Date of Patent: May 23, 2000

[54] **METHOD FOR CLONING AND EXPRESSION OF BSRFI RESTRICTION ENDONUCLEASE IN *E. COLI***

[75] Inventors: Shuang-yong Xu, Lexington; Jian-Ping Xiao, Wenham, both of Mass.

[73] Assignee: New England Biolabs, Inc., Beverly, Mass.

[21] Appl. No.: 09/307,621

[22] Filed: May 7, 1999

[51] Int. Cl.[7] ............................. C12N 9/22; C12N 15/55
[52] U.S. Cl. .................. 435/199; 435/252.3; 435/326.1; 536/23.2
[58] Field of Search ................................ 435/199, 320.1, 435/252.3; 536/23.2

[56] References Cited

U.S. PATENT DOCUMENTS

| | | | |
|---|---|---|---|
| 5,200,333 | 4/1993 | Wilson | 435/172.3 |
| 5,498,535 | 3/1996 | Fomenkov et al. | 435/172.3 |

OTHER PUBLICATIONS

Roberts and Macelis, Nucl. Acids Res. 27: 312–313, (1999).
Kosykh et al, Mol. Gen. Genet. 178: 717–719 (1980).
Mann et al, Gene 3: 97–112, (1978).
Walder et al, Proc. Nat. Acad. Sci. 78: 1503–1507,(1981).
Bougueleret et al, Nucl. Acids Res. 12: 3659–3676, (1984).
Gingeras and Brooks, Proc. Natl. Acad. Sci. USA 80: 402–406, (1983).
Theriault and Roy, Gene 19: 355–359, (1985).
Blumenthal et al, J. Bacteriol. 164: 501–509, (1985).
Wayne et al, Gene 202: 83–88, (1997).
Kiss et al, Nucl. Acids Res. 13: 6403–6421, (1985).
Szomolanyi et al, Gene 10: 219–225, (1980).
Janulaitis et al, Gene 20: 197–204, (1982).
Kiss and Baldauf, Gene 21: 111–119, (1983).
Walder et al, J. Biol. Chem. 258: 1235–1241, (1983).
Fomenkov et al, Nucl. Acids Res. 22: 2399–2403, (1994).

*Primary Examiner*—Charles L. Patterson, Jr.
*Attorney, Agent, or Firm*—Gregory D. Williams

[57] ABSTRACT

BsrFI restriction enzyme was purified from *Bacillus stearothermophilus* to near homogeneity. The protein was sequenced to obtain its N-terminus amino acid sequence. A set of denegerate primers were synthesized based on the aa sequence. The first 18 codons encoding BsrFI restriction endonuclease (bsrFIR) was amplified by PCR and its coding sequence was obtained. The methylase selection method was used to clone BsrFI methylase gene (bsrFIM). Two clones were found to be resistant to BsrFI digstion. The entire insert in one clone was sequenced and the insert encodes the BsrFI methylase (M. BsrFI). In addition, a small truncated open reading frame adjacent to the methylase gene has homology to Cfr10I restriciton endonuclease in a BlastX homology search in Genbank database. BsrFI and Cfr10I are isoschizomer that recognizes and cleaves 5'R^CCGGY3'. Two primers were used to amplify the bsrFIR gene, The forward primer is a degenerate primer designed from the N-terminus aa sequence and the reverse primer is the bona fide sequence derived from the BsrFI methylase[+] clone. The bsrFIR gene was amplified by PCR, ligated into a T7 expression vector pET21at and the ligated DNA was transformed into premodified cells ER2566 [pLG339-BsrFIM]. The final expression strain is ER2566 [pLG339-BsrFIM, pET21at-BsrFIR]. Recombinant BsrFI activity was detected in *E. coli* cell extract. BsrFI is cloned from a thermophile *Bacillus stearothermophilus*. Thus, BsrFI a thermostable enzyme and it is active at 37° C. to 65° C.

6 Claims, 3 Drawing Sheets

```
   1  ATGATAAAAGTGGCATCATTATTTTCTGGGGCAGGATTCCTGGATTTGGGGTTTACTGAA
      M  I  K  V  A  S  L  F  S  G  A  G  F  L  D  L  G  F  T  E
  61  AATGGTTTTGATATTGTTTGGGGAGCAGAGATAGTACCGGAATTTGCTAGATCACACAAT
      N  G  F  D  I  V  W  G  A  E  I  V  P  E  F  A  R  S  H  N
 121  TATAACATGCGACTTCGTTATAATCATGATATTGACAGAATTCACACTGTAGATATTGTC
      Y  N  M  R  L  R  Y  N  H  D  I  D  R  I  H  T  V  D  I  V
 181  AATGTTAGTCCTATGGATATACCACAAAATATTCGTGGTATAATTGGTGGCCCACCATGT
      N  V  S  P  M  D  I  P  Q  N  I  R  G  I  I  G  G  P  P  C
 241  CAAGACTTTTCAATTGGTAATGCTAATAATCCTGGCGTTACAGGGGAAAGGGGTAAATTG
      Q  D  F  S  I  G  N  A  N  N  P  G  V  T  G  E  R  G  K  L
 301  GTATGGAATTTTTTAGAGAAAATTGCTTATTTACAGCCTGATTTCTTTTTATTTGAAAAT
      V  W  N  F  L  E  K  I  A  Y  L  Q  P  D  F  F  L  F  E  N
 361  GTCGAGGGATTATACAAAATAAAAAAACATCGAACACAGGCTTTGTTGCCAATGCTTGAA
      V  E  G  L  Y  K  I  K  K  H  R  T  Q  A  L  L  P  M  L  E
 421  ATACTAGATGATATGAGCAAAATTAAAAACAGCGGGTTTGTAAATATTGACGGTAATATT
      I  L  D  D  M  S  K  I  K  N  S  G  F  V  N  I  D  G  N  I
 481  AATATTGAAGTTCTTGGTTATAAGACATATTTTAAAGTTCTAAATGCCTTGGAATTTGGC
      N  I  E  V  L  G  Y  K  T  Y  F  K  V  L  N  A  L  E  F  G
 541  ATTCCTCAGGATAGGACCAGAGTGTTTGTAGTAGGATTCAAAAAATCAATAATTGAAGCC
      I  P  Q  D  R  T  R  V  F  V  V  G  F  K  K  S  I  I  E  A
 601  TTACAAGAAAACAACATGGACATTTTTCAGTGGCCAACTCCAACATATCCCGATGCAAAA
      L  Q  E  N  N  M  D  I  F  Q  W  P  T  P  T  Y  P  D  A  K
 661  AACGCTTACAACTGGCCTGAGACCTGGGAATTTGGTACAAAAATAGATGAGGAAAATTTC
      N  A  Y  N  W  P  E  T  W  E  F  G  T  K  I  D  E  E  N  F
 721  ATTAAAAACTTAGATGTTCCATACGAGCTAACTGTCCATAGTGTTATTGGTAATTCGAAA
      I  K  N  L  D  V  P  Y  E  L  T  V  H  S  V  I  G  N  S  K
 781  GAACTCGAGTCCCTTCCAAACCATGTATCTTTTAATCCTAAATCTGATAAGTTTAATGTT
      E  L  E  S  L  P  N  H  V  S  F  N  P  K  S  D  K  F  N  V
 841  GTAATGGAAGGAGACACAAGCCGAAAGTCATTTAAACGACTGCATCGCTTTAGATATAGT
      V  M  E  G  D  T  S  R  K  S  F  K  R  L  H  R  F  R  Y  S
 901  CCAACTGTTGCATATGGAAATAATGAGGTGCATTTGCATCCTACGTTACCCAGAAGACTA
      P  T  V  A  Y  G  N  N  E  V  H  L  H  P  T  L  P  R  R  L
 961  ACGGTTCGTGAAGCATTAAGGCTTCAGTCTGTACCTGATTGGTATAAGTTTCCCGAAGAT
      T  V  R  E  A  L  R  L  Q  S  V  P  D  W  Y  K  F  P  E  D
1021  ATACCATTAGACAAAATGTTTAAAATGGTTAGTAATGGTGTCCCATACAAGTTAGCATTT
      I  P  L  D  K  M  F  K  M  V  S  N  G  V  P  Y  K  L  A  F
1081  TTGTTAGCAAGGCAAATTAAGAAAGTTTTAACGGATTACGATTCTTTAAACTTAAAAAAA
      L  L  A  R  Q  I  K  K  V  L  T  D  Y  D  S  L  N  L  K  K
1141  ACAAATAAGCAACTTCTTGAAATCAAATAA  1170
      T  N  K  Q  L  L  E  I  K  *
```

FIG. 3

```
    ATGATGACCGAACTTAAAAATAGTAATTGCATTGAAGAGTATCAGGAAAATGGAAAAACA
1   ------------------------------------------------------------   60
    M  M  T  E  L  K  N  S  N  C  I  E  E  Y  Q  E  N  G  K  T
    AAAGTCCGCATTAAACCATTTAACGCATTAATCGAACTTTATGATAATCAGATTCCAACA
61  ------------------------------------------------------------   120
    K  V  R  I  K  P  F  N  A  L  I  E  L  Y  D  N  Q  I  P  T
    GGAAATATTAAAGAAAACTTAGACAAACTACAAAATTACGTTATGAAGGTAGCTGACGCA
121 ------------------------------------------------------------   180
    G  N  I  K  E  N  L  D  K  L  Q  N  Y  V  M  K  V  A  D  A
    AAAGGGCTTACCAAGCCAGCTAGTGCTGCCTTTTCAAATACTCGTGGTACATGGTTCGAA
181 ------------------------------------------------------------   240
    K  G  L  T  K  P  A  S  A  A  F  S  N  T  R  G  T  W  F  E
    GTTATGATTGCTATCCAATCATGGAATTATCGGATCAAAAGGGGTTACAATGACTACCTA
241 ------------------------------------------------------------   300
    V  M  I  A  I  Q  S  W  N  Y  R  I  K  R  G  Y  N  D  Y  L
    ATTATCAAAATGCCAAATGTAAAAACTTTTGATTTCCGAAAGATCTTTGATGATGAGACA
301 ------------------------------------------------------------   360
    I  I  K  M  P  N  V  K  T  F  D  F  R  K  I  F  D  D  E  T
    AGAGAAAAACTATACCAGCTTGAAAAATCATTGTTAACACATAAACAACAGGTTAGATTA
361 ------------------------------------------------------------   420
    R  E  K  L  Y  Q  L  E  K  S  L  L  T  H  K  Q  Q  V  R  L
    ATTACCTCGAATCCCGATTTGCTAATAATTAGACAAAAAGATTTGATAAAAGATGAATAC
421 ------------------------------------------------------------   480
    I  T  S  N  P  D  L  L  I  I  R  Q  K  D  L  I  K  D  E  Y
    AATCAGCCAATAGATAAATTTACACATGAAAATGTTGATACTGCCTTAACCTTATTTAAA
481 ------------------------------------------------------------   540
    N  Q  P  I  D  K  F  T  H  E  N  V  D  T  A  L  T  L  F  K
    CATCTAGAGCGTAAGTGCAAATGGGATTCGTTAGTGGCTGGAATTGGTTTAAAAACATCG
541 ------------------------------------------------------------   600
    H  L  E  R  K  C  K  W  D  S  L  V  A  G  I  G  L  K  T  S
    TTGCGCCCTGACAGAAGACTTCAACTTGTTCATGAGGGGAACATTTTAAAATCTTTGTTT
601 ------------------------------------------------------------   660
    L  R  P  D  R  R  L  Q  L  V  H  E  G  N  I  L  K  S  L  F
    GCTCATTTAAAGATGCGTTATTGGAACCCAAAGGCAGAATTTAAATATTATGGTGCTTCA
661 ------------------------------------------------------------   720
    A  H  L  K  M  R  Y  W  N  P  K  A  E  F  K  Y  Y  G  A  S
    AGTGAACCAGTTAGTCAAGCAGACGACGACGCATTACAAACCGCAGCTACACATACAATT
721 ------------------------------------------------------------   780
    S  E  P  V  S  Q  A  D  D  D  A  L  Q  T  A  A  T  H  T  I
    GTAAATGTTAATTCTACACCTGAAAGAGCTGTTGATGATGTATTCTCATTAACCTCGTTT
781 ------------------------------------------------------------   840
    V  N  V  N  S  T  P  E  R  A  V  D  D  V  F  S  L  T  S  F
    GAAGATATTGACAAAATGTTGGATCAAATTATAAAAAAATAA
841 ----------------------------------------- 882
    E  D  I  D  K  M  L  D  Q  I  I  K  K  *
```

METHOD FOR CLONING AND EXPRESSION OF BSRFI RESTRICTION ENDONUCLEASE IN E. COLI

BACKGROUND OF THE INVENTION

The present invention relates to recombinant DNA which encodes the BsrFI restriction endonuclease as well as BsrFI methyltransferase, and production of BsrFI restriction endonuclease from *E. coli* cells containing the recombinant DNA.

Type II restriction endonucleases are a class of enzymes that occur naturally in bacteria and in some viruses. When they are purified away from other bacterial proteins, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTTAAA3', 5'PuGGNCCPy3' and 5' CACNNNGTG3' respectively. *Escherichia coli* RY13, on the other hand, produces only one enzyme, EcoRI, which recognizes the sequence 5'GAATTC3'.

A second component of bacterial restriction-modification (R-M) systems are the methyltransferase (methylases). These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

A large number of type II restriction-modification systems have been cloned. The first cloned systems used bacteriophage infection as a means of identifying or selecting restriction endonuclease clones (EcoRII: Kosykh et al., Mol. Gen. Genet. 178:717–719, (1980); HhaII: Mann et al., Gene 3:97–112, (1978); PstI: Walder et al., Proc. Nat. Acad. Sci. 78:1503–1507, (1981)). Since the presence of restriction-modification systems in bacteria enable them to resist infection by bacteriophage, cells that carry cloned restriction-modification genes can, in principle, be selectively isolated as survivors from libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acids. Res. 12:3659–3676, (1984); PaeR7: Gingeras and Brooks, Proc. Natl. Acad. Sci. USA 80:402–406, (1983); Theriault and Roy, Gene 19:355–359 (1982); PvuII: Blumenthal et al., J. Bacteriol. 164:501–509, (1985); Tsp45I: Wayne et al. Gene 202:83–88, (1997)).

A third approach, and one that is being used to clone a growing number of R-M systems are now being cloned by selection for an active methylase gene (U.S. Pat. No. 5,200, 333 and BsuRI: Kiss et al., Nucl. Acids. Res. 13:6403–6421, (1985)). Since R-M genes are often closely linked, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119, (1983); and MspI: Walder et al., J. Biol. Chem. 258:1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535, (1996); Fomenkov et al., Nucl. Acids Res. 22:2399–2403, (1994)). This method utilizes the *E. coli* SOS response following DNA damages caused by restriction endonucleases or nonspecific nucleases. A number of thermostable nuclease genes (TaqI, Tth111I, BsoBI, Tf nuclease) have been cloned by this method (U.S. Pat. No. 5,498,535, 1996).

Because purified restriction endonucleases, and to a lesser extent, modification methylases, are useful tools for creating recombinant molecules in the laboratory, there is a commercial incentive to obtain bacterial strains through recombinant DNA techniques that produce these enzymes in large quantities. Such overexpression strains would also simplify the task of enzyme purification.

SUMMARY OF THE INVENTION

BsrFI restriction enzyme was purified from *Bacillus stearothermophilus* to near homogeneity. The protein was sequenced to obtain its N-terminus amino acid (aa) sequence. A set of degenerate primers were synthesized based on the aa sequence. The first 18 codons encoding BsrFI restriction endonuclease (bsrFIR) were amplified by PCR and its coding sequence obtained. Inverse PCR was attempted to clone the adjacent coding sequence. It failed to amplify any new DNA sequences. Therefore the methylase selection method was used to clone the BsrFI methylase gene (bsrFIM). After BsrFI methylase selection (digestion of an ApoI partial library with BsrFI and retransformation), two clones were found to be resistant to BsrFI digestion. The entire insert in one clone was sequenced and the insert encodes the BsrFI methylase (M.BsrFI). In addition, a small truncated open reading frame adjacent to the methylase gene was found to have homology to the Cfr10I restriction endonuclease in a BlastX homology search in the GenBank database. BsrFI and Cfr10I are isoschizomers that recognize and cleave 5'R^CCGGY3'. Two primers were used to amplify the bsrFIR gene, The forward primer is a degenerate primer designed from the N-terminal aa sequence and the reverse primer is the bona fide sequence derived from the BsrFI methylase[+] clone. The bsrFIR gene was amplified by PCR, ligated into a T7 expression vector pET21at and the ligated DNA was transformed into premodified cells ER2566 [pLG339-BsrFIM]. The final expression strain is ER2566 [pLG339-BsrFIM, pET21at-BsrFIR]. Recombinant BsrFI activity was detected in *E. coli* cell extract. BsrFI is cloned from a thermophile *Bacillus stearothermophilus*. Thus, BsrFI is a thermostable enzyme and it is active at 37° C. to 65° C. The isoschizomer Cfr10I was cloned from a mesophilic microorganism *Citrobacter freundii* RFL10.

BRIEF DESCRIPTION OF THE DRAWINGS

FIG. 2. DNA sequence of bsrFIM gene (SEQ ID NO:1) and its encoded amino acid sequence (SEQ ID NO:2).

FIG. 3. DNA sequence of bsrFIR gene (SEQ ID NO:3) and its encoded amino acid sequence (SEQ ID NO:4).

DETAILED DESCRIPTION OF THE INVENTION

The method described herein by which the BsrFI methylase gene and the BsrFI restriction endonuclease genes are preferably cloned and expressed in *E. coli* using the following steps:

1. Preparation of genomic DNA.

Genomic DNA is prepared from *Bacillus stearothermophilus* (this strain is in the New England Biolabs' collection, NEB #695, Beverly, Mass.) by standard procedures.

2. Purification of the native BsrFI restriction enzyme

The native BsrFI restriction enzyme is purified to near homogeneity by chromatography through DNA affinity columns and ion-exchange columns. The size of the native protein is approximately 35 kDa. Purified BsrFI is subjected to electrophoresis and electroblotted to a membrane and subjected to sequential degradation on an Applied Biosystems model 407A protein sequencer.

3. PCR amplification of DNA coding sequence for N-terminal amino acid.

The N-terminus amino acid sequence is used to design three degenerate primers. The coding sequence is amplified by PCR, cloned in pUC19 and sequenced. The N-terminus coding sequence (18 codons) is obtained. Inverse PCR is carried out to amplify the upstream and downstream DNA sequences. If there are PCR products, sequence the PCR products and walk further by inverse PCR to find the methylase gene upstream. If there are no PCR products, go to step 4.

4. Construction of an ApoI partial genomic DNA library.

*Bacillus stearothermophilus* genomic DNA is digested with ApoI to achieve the desired partial digestion. The ApoI partially digested genomic DNA in the range of 2–10 kb is ligated into EcoRI cut and CIP treated vector pRRS at 16° C. overnight. Electroporation is carried out using RR1 competent cells and the ligated DNA. Transformants are pooled and amplified. Plasmid DNA is prepared from overnight cell cultures. The ApoI partial library DNA is digested with BsrFI at 37° C. overnight. The digested DNA is used to re-transform RR1 competent cells. Plasmid DNA is isolated and individual plasmid DNA is digested with BsrFI to detect resistance to digestion. Two plasmid isolates display resistance to BsrFI digestion.

5. Sequencing of the insert carrying BsrFI methylase gene

The insert in one plasmid is sequenced by primer walking. Two ApoI fragments and two BamHI-NdeI fragments are subcloned in pUC19 and sequenced. Primers are synthesized to sequence the non-overlapping region or to confirm the complementary strand of the known sequence. The entire insert is 1714 bp, encoding the BsrFI methylase and the C-terminal portion of BsrFI endonuclease (186 bp). BsrFI methylase has 343 amino acid residues with predicted molecular mass of 39,474 daltons (39.5 kDa). The bsrFIM gene DNA sequence and its predicted aa sequence are shown in FIG. 2.

6. Expression of bsrFIM gene in *E. coli*

PCR is performed to amplify the bsrFIM gene. The PCR product is digested with BamHI and ligated into BamHI cut and CIP treated pLG339 vector. The ligated DNA is transformed into RR1 competent cells. Transformants are plated on Km plates (50 μg/ml). Plasmids are screened for methylase gene inserts and two clones are found to be resistant to BsrFI digestion. The resistant plasmids are transformed into a T7 expression host ER2566.

7. Cloning and expression of bsrFIR gene in *E. coli*

Figure 1:
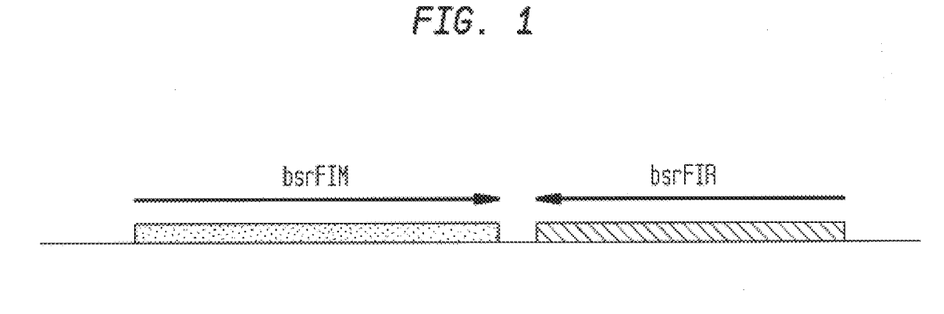
FIG. 1. Gene organization of BsrFI restriction-modification system.

The N-terminus coding sequence (18 codons) is derived by PCR as described in step 3. The C-terminal coding sequence (186 bp) is obtained from the M.BsrFI[+] clone. Two primers are used to amplify the bsrFIR gene directly from the genomic DNA. The PCR product is gel-purified from a low-melting agarose gel and sequenced directly. The bsrFIR gene is found to be 882 bp, encoding a protein with predicted molecular mass of 33,843 daltons (33.8 kDa). The gene organization of BsrFI R-M system is shown in FIG. 1.

Although the entire bsrFIR gene sequence is known, the 3rd to 7th codons are still degenerate. To obtain the bona fide sequence, inverse PCR primers are synthesized. *Bacillus stearothermophilus* genomic DNA is digested with ApoI, BspHI, HhaI, MfeI, NlaIII, or Sau3AI. The digested DNA is ligated at a low DNA concentration (2 μg/ml). Inverse PCR reactions are carried out using the above ligated genomic DNA and primers under condition of 95° C. 1', 55° C. 1', 72° C. 2' for 30 cycles. PCR products are found in ApoI, HhaI, NlaIII, and Sau3AI digested and self-ligated DNA. The PCR products are gel-purified and sequenced. The actual sequence for the first seven codons of bsrFIR gene is obtained.

Figure 4:
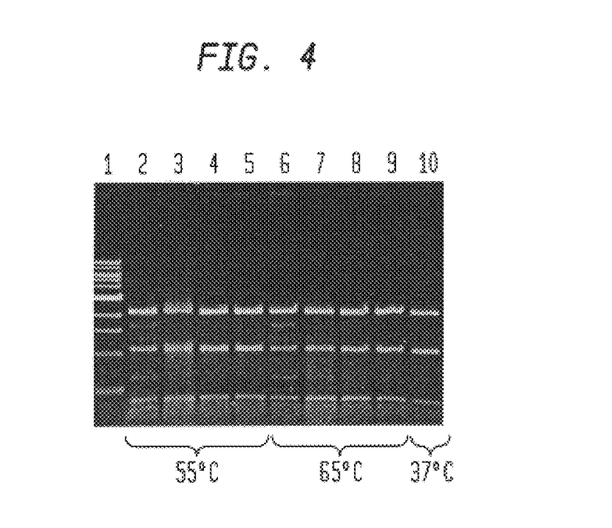
FIG. 4. Restriction digestion using *E. coli* cell extract containing recombinant BsrFI restriction endonuclease. Lanes 2, 6, and 10 were native BsrFI purified from *Bacillus stearothermophilus*. Lanes 3–5, 7–9 were recombinant BsrFI. Lanes 2–5 reactions were carried out at 55° C. Lanes 6–9 reactions were carried out at 65° C. Lane 10, reaction was carried out at 37° C. Lane 1, 1 kb DNA size marker (New England Biolabs, Inc., Beverly, Mass.).

To overexpress bsrFIR gene in *E. coli*, the bsrFIR gene is amplified by PCR. The PCR product is digested with NdeI and BamHI and ligated into BamHI-NdeI digested pET21at. The ligated DNA is transformed into ER2566 [pLG339-BsrFIM] premodified cells. Clones with PCR inserts are cultured in LB plus Amp (100 μg/ml) and Km (50 μg/ml) to late log phase and BsrFI protein production is induced by addition of IPTG to a final of 0.5 mM for 3 h. Cells are harvested by centrifugation and lysed by sonication. Cell debris is removed and cell extracts are used to assay BsrFI endonuclease activity. To demonstrate that BsrFI is a thermostable restriction enzyme, the DNA substrate pBR322 is digested with cell extract at 55° C. and 65° C., which gives rise to the same restriction pattern as the one digested at 37° C. (FIG. 4).

The present invention is further illustrated by the following Example. The Example is provided to aid in the understanding of the invention and is not construed as a limitation thereof.

The references cited above and below are herein incorporated reference.

EXAMPLE 1

Cloning of BsrFI Restriction-Modification System in *E. Coli*

1. Preparation of genomic DNA

Genomic DNA was prepared from *Bacillus stearothermophilus* (this strain is in the New England Biolabs' collection, NEB #695, Beverly, Mass.) by the standard procedure with the following steps: 1. cell lysis with lysozyme, Triton X-100, and SDS; 2. phenol-CHCl$_3$ and CHCl$_3$ extractions; 3. ethanol precipitation; 4. dialysis in TE buffer (change buffer 4 times); 5. RNase A treatment; 6. ethanol precipitation and resuspend genomic DNA in TE buffer.

2. Purification of the native BsrFI restriction enzyme

The native BsrFI restriction enzyme was purified to near homogeneity by chromatography through DNA affinity columns and ion-exchange columns. The size of the native protein is approximately 35 kDa on SDS-PAGE. Purified BsrFI was subjected to electrophoresis and electroblotted to a membrane. The membrane was stained with Coomassie brilliant blue R-250, and the protein band of approximately 35 kDa was excised and subjected to sequential degradation on an Applied Biosystems model 407A prtoein sequencer. The N-terminus has the following amino sequence:
MMTELKNSNXIEEYQENGKTKV (X=unknown amino acid) (SEQ ID NO:5).

3. PCR amplification of the N-terminal DNA coding sequence

The amino acid sequence MMTELKN was used to design the following two degenerate primers:
5'ATGATGACNGARTTRAARAA 3' 166–170 (N=A,C,G, T; R=A,G). (SEQ ID NO:6)
5'ATGATGACNGARCTNAARAA 3' 166–171 (SEQ ID NO:7) (Leu codons could be TTR or CTN)

The amino acid sequence EYQENGK (SEQ ID NO:8) was used to synthesize the following degenerate primer:
5'TTNCCRTTYTCYTGRTAYTC 3' 166–172 (SEQ ID NO:9) (This primer is a complement of 5'GARTAYCAR-GARAAYGGNAA 3' (SEQ ID NO:10)).

Primers 166–170 and 166–172 in reaction 1, primers 166–171 and 166–172 in reaction 2 were used to amplify the first 18 codons of bsrFIR gene. The following PCR conditions were used: 95° C. 1', 40° C. 1', 72° C. 30" for 30 cycles. The PCR product was gel-purified from a 3.5% low-melting agarose gel. After β-agarase treatment and ethanol precipitation, the PCR product was treated with T4 polynucleotide kinase and ligated to HincII cut and CIP treated pUC19. Plasmids with the correct size inserts were found and the inserts were sequenced with pUC19 universal primers. Three different coding sequences were obtained, each coding for the correct aa sequence.

These three sequences are:
5'ATGATGAC<u>A</u>GA GTT <u>G</u>AAGAATAGTAATTGCATTGAAGAATA<u>C</u>CA GGAGAACGG CAA3' (SEQ ID NO:11)
M M T E L K N S N C I E E Y Q E N G X (SEQ ID NO:12)
5' ATGATGAC<u>GG</u>AG<u>TT</u> <u>A</u>AAGAATAGTAATTGCATTGAAGAGTA<u>C</u>CA GGAGAACGG CAA3' (SEQ ID NO:13)
M M T E L K N S N C I E E Y Q E N G X (SEQ ID NO:14)
5'ATGATGAC<u>AGAACT</u> <u>G</u>AAGAATAGTAATTGCATTGAAGAGTA<u>T</u>CA <u>A</u>GAGAACGG CAA3' (SEQ ID NO:15)
M M T E L K N S N C I E E Y Q E N G X (SEQ ID NO:16)

(The underlined bases are degenerate). Amongst all three sequences, codons 6 to 12 are the actual sequence amplified from the genomic DNA.

Two inverse PCR primers were designed to amplify the adjacent DNA. The inverse PCR primers have the following sequence:
5'GARTAYCARGAGAACGGCAA 3' (SEQ ID NO:17)
5'TTCAATGCAATTACTATTCTT 3' (SEQ ID NO:18)

*Bacillus stearothermophilus* genomic DNA was digested with AatII, AflII, AflIII, ApaLI, ApoI, BamHI, BglII, BspDI, BspEI, BspHI, ClaI, or EcoRI. The digested DNA was then extracted by equal volumes of phenol-CHCl$_3$ and CHCl$_3$, precipitated with cold ethanol, dried and resuspended in TE buffer. Two μg of the DNA was self-ligated with T4 DNA ligase and then extracted with phenol-CHCl$_3$ and CHCl$_3$, precipitated with cold ethanol. Inverse PCR reactions were carried out using the above ligated genomic DNA and primers under condition of 95° C. 1', 55° C. 1', 72° C. 2' for 30 cycles. No PCR products were detected. As described later, the N-terminal coding region would be used to amplify the entire bsrFIR gene once the C-terminus coding region had been cloned.

4. Construction of an ApoI partial genomic DNA library

Five μg of *Bacillus stearothermophilus* genomic DNA was digested with 2, 1, 0.5, 0.25 and 0.125 units of ApoI at 50° C. for 30 min. The ApoI partially digested genomic DNA in the range of 2–10 kb was gel-purified. The ApoI partially digested genomic DNA was ligated into EcoRI cut and CIP treated vector pRRS at 16° C. overnight. After the ligation reaction, the ligase was inactivated at 65° C. for 30 min. The ligated DNA was dialyzed by drop dialysis on a membrane on top of 2 liters of sdH$_2$O. The DNA was transfered into RR1 (TonA$^-$, DnaseI$^-$) competent cells by electroporation. Transformants were plated on LB agar plus Amp (100 μg/ml). About 10,000 colonies were obtained in the electroporation. All the transformants were pooled and inoculated into 1 liter of LB broth plus Amp and incubated at 37° C. overnight. Plasmid DNA was prepared from the overnight cells by Qiagen Maxi-prep column.

5. Challenge the ApoI partial library DNA with BsrFI digestion and cloning of BsrFI methylase gene (bsrFIM)

One and 3 μg of the ApoI partial library DNA was digested with 30 units of BsrFI at 370C overnight. The digested DNA was used to re-transform RR1 (TonA$^-$, DnaseI$^-$) competent cells. About 125 survivors were obtained. Plasmid DNA was prepared from 1.5 ml cell culture of 36 transformants. Individual plasmid DNA was digested with BsrFI to detect any resistance to digestion. Two plasmids isolated, #6 and #31 displayed resistance to BsrFI digestion, suggesting that the cloned BsrFI methylase gene was completely cloned and expressed in *E. coli* (sequencing the insert verified that the entire BsrFI methylase gene was cloned, see below).

6. Sequencing of the insert carrying BsrFI methylase gene

The insert in #6 plasmid was sequenced by primer walking using AmpliTaq DNA polymerase dideoxy terminator sequencing kit and ABI373A automated DNA sequencer. Primers were synthesized to sequence the non-overlapping region or to confirm the complementary strand of the known sequence. Two ApoI fragments and two BamHI-NdeI fragments were subcloned in pUC19 and sequenced. The entire insert is 1714 bp, encoding the BsrFI methylase and the C-terminal portion of BsrFI endonuclease (186 bp). BsrFI methylase contains 343 aa residues with predicted molecular mass of 39,474 daltons (39.5 kDa). The gene organization of BsrFI R-M system is shown in FIG. 1. The bsrFIM gene DNA sequence and its predicted aa sequence are shown in FIG. 2.

7. Expression of bsrFIM gene in *E. coli*

PCR was performed to amplify the bsrFIM gene. BamHI sites were engineered into the two primers at the 5' ends. The PCR primers have the following sequence:

5'GTGGGATCCGCATGCGGAGG-
TAAAAAAATGATAAAAGTGGCATCATTATTTTCT3' (200-67) (SEQ ID NO:19)

5'GTGGGATCCGCATGCT-
TATTTGATTTCAAGAAGTTGCTTATTTGTTTT3' (200-68). (SEQ ID NO:20)

PCR reactions were performed in a total volume of 100 μl using 0.2 μg genomic DNA, 10 μl 10× Thermopol buffer, 0.27 mM concentration of DNTP, 79 μl H$_2$O, 0.24 μg of primer 200-67 and 200-68 (2.4 μg/ml final), 2 units of Vent® DNA polymerase, with 2, 4, 6, and 8 mM Mg$^{++}$. PCR was performed at 95° C. 1', 60° C. 1', and 72° C. for 1.5' for 20 cycles. The PCR product was digested with BamHI and ligated into BamHI cut and CIP treated pLG339 vector (pSC101 replication origin). The ligated DNA was transformed into RR1 competent cells. Transformants were plated on Km plates (50 μg/ml). Eighteen plasmids were screened for inserts and two clones were found to be completely resistant to BsrFI digestion.

8. Cloning and expression of bsrFIR gene in *E. coli*

The N-terminus coding sequence (18 codons) of bsrFIR gene had been derived by PCR as described in section 3. The C-terminal coding sequence (186 bp) of bsrFIR gene was obtained from the M.BsrFI+clone. Two primers were used to amplify the bsrFIR gene directly from the genomic DNA. The primers have the following sequence:

5'ATGATGACNGARTTRAARAA3' 166-170 (SEQ ID NO:21)

5'TGTGGATCCTCCTGTATAATACCAAGAGGCTTA3' 199-108 (SEQ ID NO:22)

PCR was performed at 95° C. 1', 50° C. 1', 72° C. 1' for 30 cycles. PCR product was gel-purified from a low-melting agarose gel and sequenced directly using primers 166-170 or 199-108. The bsrFIR gene was found to be 882 bp, encoding a protein with molecular mass of 33,843 daltons (33.8 kDa). The bsrFIR gene sequence and its encoded aa sequence are shown in FIG. 3.

Although the entire bsrFIR gene sequence is known, the 3rd to 7th codons were still degenerate. To obtain the bona fide sequence, inverse PCR primers were synthesized. The primers have the following sequence:

5'AAGTTCGATTAATGCGTTAAATGG3' (207-56) (SEQ ID NO:23)

5'TATGATAATCAGATTCCAACAGGA3' (207-57) (SEQ ID NO:24)

*Bacillus stearothermophilus* genomic DNA was digested with ApoI, BspHI, HhaI, MfeI, NlaIII, or Sau3AI. The digested DNA was ligated at a low DNA concentration (2 μg/ml). Inverse PCR reactions were carried out using the above ligated genomic DNA and primers under condition of 95° C. 1', 55° C. 1', 72° C. 2' for 30 cycles. PCR products were found in ApoI, HhaI, NlaIII, and Sau3AI digested and self-ligated DNA. The PCR products were gel-purified from a low-melting agarose gel and sequenced directly using primers 207-56 and 207-57. The degenerate sequence and the actual sequence for the first seven codons of bsrFIR gene are shown below:

5'ATGATGACNGARTTRAARAA3' (166-170) (SEQ ID NO:25)

5'ATGATGACNGARCTNAARAA3' (166-171) (SEQ ID NO:26)

5'ATGATGACCGAACTTAAAAA3' (SEQ ID NO:27) (bona fide coding sequence)

M M T E L K N (SEQ ID NO:28)

To overexpress bsrFIR gene in *E. coli*, two primers with the following sequences were synthesized:

5'GGAGGAGTCCATATGATGACCGAACT<u>G</u>AAAAA
CTCCAA<u>C</u>TGCATTGAAGAGTA
T3' (208-128 (SEQ ID NO:29) (Underlined bases are base substitutions to increase codon usage in *E. coli*. Leu codon, CTT to CTG; Asn codon, AAT to AAC; Ser codon, AGT to TCC, Asn codon AAT to AAC)

5'GGAGGATCCTTATTTTTT-
TATAATTTGATCCAACATTTTGTCAAT3' (203-96). (SEQ ID NO:30)

PCR reactions were performed using 0.2 μg genomic DNA, 10 μl 10 X Thermopol buffer, 0.27 mM concentration of DNTP, 79 μl H$_2$O, 0.24 μg of primers 208-128 and 20396, 2 units of Vent® DNA polymerase, with 2, 4, 6, 8, and 10 mM Mg$^{++}$ in a total volume of 100 μl. PCR thermocycling conditions were 95° C. 1', 60° C. 1', and 72° C., 1' for 20 cycles. The PCR product was digested with NdeI and BamHI and ligated into BamHI-NdeI digested pET21at. The ligated DNA was transformed into ER2566 [pLG339-BsrFIM] premodified cells. Eighteen transformants were screened for inserts. Nine out of 18 had PCR insert. These nine clones were cultured in LB plus Amp (100 μg/ml) and Km (50 μg/ml) to late log phase and BsrFI protein production was induced by addition of IPTG to a final of 0.5 mM for 3 h. Cells were harvested by centrifugation and lysed by sonication. Cell debris was removed by centrifugation and cell extracts were used to assay BsrFI endonuclease activity. Five out of nine extracts displayed BsrFI activity. To demonstrate that BsrFI is a thermostable restriction enzyme, the DNA substrate pBR322 was digested with 0.5, 1 and 2 μl of cell extact at 55° C. and 65° C., which gave rise to the same restriction pattern as the one digested at 37° C. (see FIG. 4 for details). The *E. coli* strain ER2566 [pLG339-BsrFIM, pET21at-BsrFIR] has been deposited with the American Type Culture Collection on May 7, 1999 and received Accession No. PTA-28.

What is claimed is:

1. Isolated DNA coding for the BsrFI restriction endonuclease, wherein the isolated DNA is obtainable from *Bacillus stearothermophilus*.

2. A recombinant DNA vector comprising a vector into which a DNA segment encoding the BsrFI restriction endonuclease has been inserted.

3. Isolated DNA encoding the BsrFI restriction endonuclease and methylase, wherein the isolated DNA is obtainable from ATCC No. PTA-28.

4. A cloning vector which comprises the isolated DNA of claim 3.

5. A host cell transformed by the vector of claim 2 or 4.

6. A method of producing recombinant BsrFI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO. : 6,066,487

DATED : May 23, 2000

INVENTOR(S) : Shuang-yong Xu and Jian-Ping Xiao

Page 1 of 2

It is certified that error appears in the above-indentified patent and that said Letters Patent is hereby corrected as shown below:

On the title page:

In the Abstract

Line 9                replace "digstion" with --digestion--
Line 16               replace "gene," with --gene.--

Column 1, line 30     after "*radiophilus*" insert --,--
Column 2, line 3      after "719" delete ","
Column 2, line 4      after "112" delete ","
Column 2, line 5      after "1507" delete ","
Column 2, line 17     after "3676" delete ","
Column 2, line 18     after "406" delete ","
Column 2, line 20     after "509" delete ","
Column 2, line 20     after "et al." insert --,--
Column 2, line 21     after "88" delete ","
Column 2, line 25     after "6421" delete ","
Column 2, line 30     after "225" delete ","
Column 2, line 32     after "119" delete ","
Column 2, line 33     after "1241" delete ","
Column 2, line 38     after "5,498,535" delete ","
Column 2, line 39     after "2403" delete ","
Column 2, line 44     replace "1996)" with --(1996))--
Column 3, line 8      replace "gene," with --gene.--

UNITED STATES PATENT AND TRADEMARK OFFICE
CERTIFICATE OF CORRECTION

PATENT NO. : 6,066,487
DATED : May 23, 2000
INVENTOR(S) : Shuang-yong Xu and Jian-Ping Xiao It is certified that error appears in the above-indentified patent and that said Letters Patent is hereby corrected as shown below:

Column 6, line 57    replace "370C" with --37°C--
Column 7, line 28    replace "DNTP" with --dNTP--
Column 8, line 39    replace "DNTP" with --dNTP--
Column 8, Line 39    replace "20396" with --203-96--

Signed and Sealed this

Thirteenth Day of March, 2001

Attest:

NICHOLAS P. GODICI

Attesting Officer     Acting Director of the United States Patent and Trademark Office

SEQUENCE LISTING

<160> NUMBER OF SEQ ID NOS: 30

<210> SEQ ID NO 1
<211> LENGTH: 1170
<212> TYPE: DNA
<213> ORGANISM: Bacillus stearothermophilus
<220> FEATURE:
<221> NAME/KEY: CDS
<222> LOCATION: (1)..(1167)

<400> SEQUENCE: 1

```
atg ata aaa gtg gca tca tta ttt tct ggg gca gga ttc ctg gat ttg        48
Met Ile Lys Val Ala Ser Leu Phe Ser Gly Ala Gly Phe Leu Asp Leu
 1               5                  10                  15 ggg ttt act gaa aat ggt ttt gat att gtt tgg gga gca gag ata gta        96
Gly Phe Thr Glu Asn Gly Phe Asp Ile Val Trp Gly Ala Glu Ile Val
                20                  25                  30 ccg gaa ttt gct aga tca cac aat tat aac atg cga ctt cgt tat aat       144
Pro Glu Phe Ala Arg Ser His Asn Tyr Asn Met Arg Leu Arg Tyr Asn
            35                  40                  45 cat gat att gac aga att cac act gta gat att gtc aat gtt agt cct       192
His Asp Ile Asp Arg Ile His Thr Val Asp Ile Val Asn Val Ser Pro
        50                  55                  60 atg gat ata cca caa aat att cgt ggt ata att ggt ggc cca cca tgt       240
Met Asp Ile Pro Gln Asn Ile Arg Gly Ile Ile Gly Gly Pro Pro Cys
 65                  70                  75                  80 caa gac ttt tca att ggt aat gct aat aat cct ggc gtt aca ggg gaa       288
Gln Asp Phe Ser Ile Gly Asn Ala Asn Asn Pro Gly Val Thr Gly Glu
                85                  90                  95 agg ggt aaa ttg gta tgg aat ttt tta gag aaa att gct tat tta cag       336
Arg Gly Lys Leu Val Trp Asn Phe Leu Glu Lys Ile Ala Tyr Leu Gln
               100                 105                 110 cct gat ttc ttt tta ttt gaa aat gtc gag gga tta tac aaa ata aaa       384
Pro Asp Phe Phe Leu Phe Glu Asn Val Glu Gly Leu Tyr Lys Ile Lys
           115                 120                 125 aaa cat cga aca cag gct ttg ttg cca atg ctt gaa ata cta gat gat       432
Lys His Arg Thr Gln Ala Leu Leu Pro Met Leu Glu Ile Leu Asp Asp
       130                 135                 140 atg agc aaa att aaa aac agc ggg ttt gta aat att gac ggt aat att       480
Met Ser Lys Ile Lys Asn Ser Gly Phe Val Asn Ile Asp Gly Asn Ile
145                 150                 155                 160 aat att gaa gtt ctt ggt tat aag aca tat ttt aaa gtt cta aat gcc       528
Asn Ile Glu Val Leu Gly Tyr Lys Thr Tyr Phe Lys Val Leu Asn Ala
                165                 170                 175 ttg gaa ttt ggc att cct cag gat agg acc aga gtg ttt gta gta gga       576
Leu Glu Phe Gly Ile Pro Gln Asp Arg Thr Arg Val Phe Val Val Gly
            180                 185                 190 ttc aaa aaa tca ata att gaa gcc tta caa gaa aac aac atg gac att       624
Phe Lys Lys Ser Ile Ile Glu Ala Leu Gln Glu Asn Asn Met Asp Ile
        195                 200                 205 ttt cag tgg cca act cca aca tat ccc gat gca aaa aac gct tac aac       672
Phe Gln Trp Pro Thr Pro Thr Tyr Pro Asp Ala Lys Asn Ala Tyr Asn
    210                 215                 220 tgg cct gag acc tgg gaa ttt ggt aca aaa ata gat gag gaa aat ttc       720
Trp Pro Glu Thr Trp Glu Phe Gly Thr Lys Ile Asp Glu Glu Asn Phe
225                 230                 235                 240 att aaa aac tta gat gtt cca tac gag cta act gtc cat agt gtt att       768
Ile Lys Asn Leu Asp Val Pro Tyr Glu Leu Thr Val His Ser Val Ile
                245                 250                 255
```

```
ggt aat tcg aaa gaa ctc gag tcc ctt cca aac cat gta tct ttt aat    816
Gly Asn Ser Lys Glu Leu Glu Ser Leu Pro Asn His Val Ser Phe Asn
        260                 265                 270 cct aaa tct gat aag ttt aat gtt gta atg gaa gga gac aca agc cga    864
Pro Lys Ser Asp Lys Phe Asn Val Val Met Glu Gly Asp Thr Ser Arg
        275                 280                 285 aag tca ttt aaa cga ctg cat cgc ttt aga tat agt cca act gtt gca    912
Lys Ser Phe Lys Arg Leu His Arg Phe Arg Tyr Ser Pro Thr Val Ala
        290                 295                 300 tat gga aat aat gag gtg cat ttg cat cct acg tta ccc aga aga cta    960
Tyr Gly Asn Asn Glu Val His Leu His Pro Thr Leu Pro Arg Arg Leu
305                 310                 315                 320 acg gtt cgt gaa gca tta agg ctt cag tct gta cct gat tgg tat aag   1008
Thr Val Arg Glu Ala Leu Arg Leu Gln Ser Val Pro Asp Trp Tyr Lys
            325                 330                 335 ttt ccc gaa gat ata cca tta gac aaa atg ttt aaa atg gtt agt aat   1056
Phe Pro Glu Asp Ile Pro Leu Asp Lys Met Phe Lys Met Val Ser Asn
            340                 345                 350 ggt gtc cca tac aag tta gca ttt ttg tta gca agg caa att aag aaa   1104
Gly Val Pro Tyr Lys Leu Ala Phe Leu Leu Ala Arg Gln Ile Lys Lys
            355                 360                 365 gtt tta acg gat tac gat tct tta aac tta aaa aaa aca aat aag caa   1152
Val Leu Thr Asp Tyr Asp Ser Leu Asn Leu Lys Lys Thr Asn Lys Gln
370                 375                 380 ctt ctt gaa atc aaa taa                                            1170
Leu Leu Glu Ile Lys
385

<210> SEQ ID NO 2
<211> LENGTH: 389
<212> TYPE: PRT
<213> ORGANISM: Bacillus stearothermophilus

<400> SEQUENCE: 2

Met Ile Lys Val Ala Ser Leu Phe Ser Gly Ala Gly Phe Leu Asp Leu
 1               5                  10                  15

Gly Phe Thr Glu Asn Gly Phe Asp Ile Val Trp Gly Ala Glu Ile Val
            20                  25                  30

Pro Glu Phe Ala Arg Ser His Asn Tyr Asn Met Arg Leu Arg Tyr Asn
        35                  40                  45

His Asp Ile Asp Arg Ile His Thr Val Asp Ile Val Asn Val Ser Pro
    50                  55                  60

Met Asp Ile Pro Gln Asn Ile Arg Gly Ile Ile Gly Pro Pro Cys
 65                 70                  75                  80

Gln Asp Phe Ser Ile Gly Asn Ala Asn Asn Pro Gly Val Thr Gly Glu
                85                  90                  95

Arg Gly Lys Leu Val Trp Asn Phe Leu Glu Lys Ile Ala Tyr Leu Gln
            100                 105                 110

Pro Asp Phe Phe Leu Phe Glu Asn Val Glu Gly Leu Tyr Lys Ile Lys
        115                 120                 125

Lys His Arg Thr Gln Ala Leu Leu Pro Met Leu Glu Ile Leu Asp Asp
    130                 135                 140

Met Ser Lys Ile Lys Asn Ser Gly Phe Val Asn Ile Asp Gly Asn Ile
145                 150                 155                 160

Asn Ile Glu Val Leu Gly Tyr Lys Thr Tyr Phe Lys Val Leu Asn Ala
                165                 170                 175

Leu Glu Phe Gly Ile Pro Gln Asp Arg Thr Arg Val Phe Val Val Gly
            180                 185                 190
```

```
Phe Lys Lys Ser Ile Ile Glu Ala Leu Gln Glu Asn Asn Met Asp Ile
            195                 200                 205

Phe Gln Trp Pro Thr Pro Thr Tyr Pro Asp Ala Lys Asn Ala Tyr Asn
            210                 215                 220

Trp Pro Glu Thr Trp Glu Phe Gly Thr Lys Ile Asp Glu Glu Asn Phe
225                 230                 235                 240

Ile Lys Asn Leu Asp Val Pro Tyr Glu Leu Thr Val His Ser Val Ile
                245                 250                 255

Gly Asn Ser Lys Glu Leu Glu Ser Leu Pro Asn His Val Ser Phe Asn
            260                 265                 270

Pro Lys Ser Asp Lys Phe Asn Val Val Met Glu Gly Asp Thr Ser Arg
            275                 280                 285

Lys Ser Phe Lys Arg Leu His Arg Phe Arg Tyr Ser Pro Thr Val Ala
290                 295                 300

Tyr Gly Asn Asn Glu Val His Leu His Pro Thr Leu Pro Arg Arg Leu
305                 310                 315                 320

Thr Val Arg Glu Ala Leu Arg Leu Gln Ser Val Pro Asp Trp Tyr Lys
                325                 330                 335

Phe Pro Glu Asp Ile Pro Leu Asp Lys Met Phe Lys Met Val Ser Asn
            340                 345                 350

Gly Val Pro Tyr Lys Leu Ala Phe Leu Leu Ala Arg Gln Ile Lys Lys
            355                 360                 365

Val Leu Thr Asp Tyr Asp Ser Leu Asn Leu Lys Lys Thr Asn Lys Gln
            370                 375                 380

Leu Leu Glu Ile Lys
385

<210> SEQ ID NO 3
<211> LENGTH: 882
<212> TYPE: DNA
<213> ORGANISM: Bacillus stearothermophilus
<220> FEATURE:
<221> NAME/KEY: CDS
<222> LOCATION: (1)..(879)

<400> SEQUENCE: 3 atg atg acc gaa ctt aaa aat agt aat tgc att gaa gag tat cag gaa      48
Met Met Thr Glu Leu Lys Asn Ser Asn Cys Ile Glu Glu Tyr Gln Glu
  1               5                  10                  15 aat gga aaa aca aaa gtc cgc att aaa cca ttt aac gca tta atc gaa     96
Asn Gly Lys Thr Lys Val Arg Ile Lys Pro Phe Asn Ala Leu Ile Glu
             20                  25                  30 ctt tat gat aat cag att cca aca gga aat att aaa gaa aac tta gac    144
Leu Tyr Asp Asn Gln Ile Pro Thr Gly Asn Ile Lys Glu Asn Leu Asp
         35                  40                  45 aaa cta caa aat tac gtt atg aag gta gct gac gca aaa ggg ctt acc    192
Lys Leu Gln Asn Tyr Val Met Lys Val Ala Asp Ala Lys Gly Leu Thr
     50                  55                  60 aag cca gct agt gct gcc ttt tca aat act cgt ggt aca tgg ttc gaa    240
Lys Pro Ala Ser Ala Ala Phe Ser Asn Thr Arg Gly Thr Trp Phe Glu
 65                  70                  75                  80 gtt atg att gct atc caa tca tgg aat tat cgg atc aaa agg ggt tac    288
Val Met Ile Ala Ile Gln Ser Trp Asn Tyr Arg Ile Lys Arg Gly Tyr
                 85                  90                  95 aat gac tac cta att atc aaa atg cca aat gta aaa act ttt gat ttc    336
Asn Asp Tyr Leu Ile Ile Lys Met Pro Asn Val Lys Thr Phe Asp Phe
            100                 105                 110
```

```
cga aag atc ttt gat gat gag aca aga gaa aaa cta tac cag ctt gaa      384
Arg Lys Ile Phe Asp Asp Glu Thr Arg Glu Lys Leu Tyr Gln Leu Glu
        115                 120                 125 aaa tca ttg tta aca cat aaa caa cag gtt aga tta att acc tcg aat      432
Lys Ser Leu Leu Thr His Lys Gln Gln Val Arg Leu Ile Thr Ser Asn
130                 135                 140 ccc gat ttg cta ata att aga caa aaa gat ttg ata aaa gat gaa tac      480
Pro Asp Leu Leu Ile Ile Arg Gln Lys Asp Leu Ile Lys Asp Glu Tyr
145                 150                 155                 160 aat cag cca ata gat aaa ttt aca cat gaa aat gtt gat act gcc tta      528
Asn Gln Pro Ile Asp Lys Phe Thr His Glu Asn Val Asp Thr Ala Leu
        165                 170                 175 acc tta ttt aaa cat cta gag cgt aag tgc aaa tgg gat tcg tta gtg      576
Thr Leu Phe Lys His Leu Glu Arg Lys Cys Lys Trp Asp Ser Leu Val
        180                 185                 190 gct gga att ggt tta aaa aca tcg ttg cgc cct gac aga aga ctt caa      624
Ala Gly Ile Gly Leu Lys Thr Ser Leu Arg Pro Asp Arg Arg Leu Gln
        195                 200                 205 ctt gtt cat gag ggg aac att tta aaa tct ttg ttt gct cat tta aag      672
Leu Val His Glu Gly Asn Ile Leu Lys Ser Leu Phe Ala His Leu Lys
210                 215                 220 atg cgt tat tgg aac cca aag gca gaa ttt aaa tat tat ggt gct tca      720
Met Arg Tyr Trp Asn Pro Lys Ala Glu Phe Lys Tyr Tyr Gly Ala Ser
225                 230                 235                 240 agt gaa cca gtt agt caa gca gac gac gac gca tta caa acc gca gct      768
Ser Glu Pro Val Ser Gln Ala Asp Asp Asp Ala Leu Gln Thr Ala Ala
                245                 250                 255 aca cat aca att gta aat gtt aat tct aca cct gaa aga gct gtt gat      816
Thr His Thr Ile Val Asn Val Asn Ser Thr Pro Glu Arg Ala Val Asp
            260                 265                 270 gat gta ttc tca tta acc tcg ttt gaa gat att gac aaa atg ttg gat      864
Asp Val Phe Ser Leu Thr Ser Phe Glu Asp Ile Asp Lys Met Leu Asp
        275                 280                 285 caa att ata aaa aaa taa                                              882
Gln Ile Ile Lys Lys
        290

<210> SEQ ID NO 4
<211> LENGTH: 293
<212> TYPE: PRT
<213> ORGANISM: Bacillus stearothermophilus

<400> SEQUENCE: 4

Met Met Thr Glu Leu Lys Asn Ser Asn Cys Ile Glu Glu Tyr Gln Glu
1               5                   10                  15

Asn Gly Lys Thr Lys Val Arg Ile Lys Pro Phe Asn Ala Leu Ile Glu
            20                  25                  30

Leu Tyr Asp Asn Gln Ile Pro Thr Gly Asn Ile Lys Glu Asn Leu Asp
        35                  40                  45

Lys Leu Gln Asn Tyr Val Met Lys Val Ala Asp Ala Lys Gly Leu Thr
    50                  55                  60

Lys Pro Ala Ser Ala Ala Phe Ser Asn Thr Arg Gly Thr Trp Phe Glu
65                  70                  75                  80

Val Met Ile Ala Ile Gln Ser Trp Asn Tyr Arg Ile Lys Arg Gly Tyr
                85                  90                  95

Asn Asp Tyr Leu Ile Ile Lys Met Pro Asn Val Lys Thr Phe Asp Phe
            100                 105                 110

Arg Lys Ile Phe Asp Asp Glu Thr Arg Glu Lys Leu Tyr Gln Leu Glu
        115                 120                 125
```

-continued

```
Lys Ser Leu Leu Thr His Lys Gln Gln Val Arg Leu Ile Thr Ser Asn
    130                 135                 140
Pro Asp Leu Leu Ile Ile Arg Gln Lys Asp Leu Ile Lys Asp Glu Tyr
145                 150                 155                 160
Asn Gln Pro Ile Asp Lys Phe Thr His Glu Asn Val Asp Thr Ala Leu
                165                 170                 175
Thr Leu Phe Lys His Leu Glu Arg Lys Cys Lys Trp Asp Ser Leu Val
            180                 185                 190
Ala Gly Ile Gly Leu Lys Thr Ser Leu Arg Pro Asp Arg Arg Leu Gln
        195                 200                 205
Leu Val His Glu Gly Asn Ile Leu Lys Ser Leu Phe Ala His Leu Lys
    210                 215                 220
Met Arg Tyr Trp Asn Pro Lys Ala Glu Phe Lys Tyr Tyr Gly Ala Ser
225                 230                 235                 240
Ser Glu Pro Val Ser Gln Ala Asp Asp Asp Ala Leu Gln Thr Ala Ala
                245                 250                 255
Thr His Thr Ile Val Asn Val Asn Ser Thr Pro Glu Arg Ala Val Asp
            260                 265                 270
Asp Val Phe Ser Leu Thr Ser Phe Glu Asp Ile Asp Lys Met Leu Asp
        275                 280                 285
Gln Ile Ile Lys Lys
    290

<210> SEQ ID NO 5
<211> LENGTH: 22
<212> TYPE: PRT
<213> ORGANISM: Bacillus stearothermophilus

<400> SEQUENCE: 5

Met Met Thr Glu Leu Lys Asn Ser Asn Xaa Ile Glu Glu Tyr Gln Glu
1               5                   10                  15
Asn Gly Lys Thr Lys Val
            20

<210> SEQ ID NO 6
<211> LENGTH: 20
<212> TYPE: DNA
<213> ORGANISM: Bacillus stearothermophilus
<220> FEATURE:
<223> OTHER INFORMATION: N=A, C, G, T ; R=A,G

<400> SEQUENCE: 6
atgatgacng arttraaraa                                                   20

<210> SEQ ID NO 7
<211> LENGTH: 20
<212> TYPE: DNA
<213> ORGANISM: Bacillus stearothermophilus
<220> FEATURE:
<223> OTHER INFORMATION: N=A,C,G,T; R=A,G

<400> SEQUENCE: 7
atgatgacng arctnaaraa                                                   20

<210> SEQ ID NO 8
<211> LENGTH: 20
<212> TYPE: DNA
<213> ORGANISM: Bacillus stearothermophilus
<220> FEATURE:
<223> OTHER INFORMATION: N=A,C,G,T; R=A,G
```

-continued

```
<400> SEQUENCE: 8
atgatgacng arctnaaraa                                              20

<210> SEQ ID NO 9
<211> LENGTH: 20
<212> TYPE: DNA
<213> ORGANISM: Bacillus stearothermophilus
<220> FEATURE:
<223> OTHER INFORMATION: N=A,C,G,T; R=A,G; Y=C or T

<400> SEQUENCE: 9
ttnccrttyt cytgrtaytc                                              20

<210> SEQ ID NO 10
<211> LENGTH: 20
<212> TYPE: DNA
<213> ORGANISM: Bacillus stearothermophilus
<220> FEATURE:
<223> OTHER INFORMATION: N=A,C,G,T; R=A,G; Y=C or T

<400> SEQUENCE: 10
gartaycarg araayggnaa                                              20

<210> SEQ ID NO 11
<211> LENGTH: 56
<212> TYPE: DNA
<213> ORGANISM: Bacillus stearothermophilus

<400> SEQUENCE: 11
atgatgacag agttgaagaa tagtaattgc attgaagaat accaggagaa cggcaa      56

<210> SEQ ID NO 12
<211> LENGTH: 19
<212> TYPE: PRT
<213> ORGANISM: Bacillus stearothermophilus

<400> SEQUENCE: 12

Met Met Thr Glu Leu Lys Asn Ser Asn Cys Ile Glu Glu Tyr Gln Glu
 1               5                  10                  15

Asn Gly Xaa

<210> SEQ ID NO 13
<211> LENGTH: 56
<212> TYPE: DNA
<213> ORGANISM: Bacillus stearothermophilus

<400> SEQUENCE: 13
atgatgacgg agttaaagaa tagtaattgc attgaagagt accaggagaa cggcaa      56

<210> SEQ ID NO 14
<211> LENGTH: 19
<212> TYPE: PRT
<213> ORGANISM: Bacillus stearothermophilus

<400> SEQUENCE: 14

Met Met Thr Glu Leu Lys Asn Ser Asn Cys Ile Glu Glu Tyr Gln Glu
 1               5                  10                  15

Asn Gly Xaa

<210> SEQ ID NO 15
<211> LENGTH: 56
<212> TYPE: DNA
```

<213> ORGANISM: Bacillus stearothermophilus

<400> SEQUENCE: 15
atgatgacag aactgaagaa tagtaattgc attgaagagt atcaagagaa cggcaa     56

<210> SEQ ID NO 16
<211> LENGTH: 19
<212> TYPE: PRT
<213> ORGANISM: Bacillus stearothermophilus

<400> SEQUENCE: 16

Met Met Thr Glu Leu Lys Asn Ser Asn Cys Ile Glu Glu Tyr Gln Glu
 1               5                  10                  15

Asn Gly Xaa

<210> SEQ ID NO 17
<211> LENGTH: 20
<212> TYPE: DNA
<213> ORGANISM: Bacillus stearothermophilus
<220> FEATURE:
<223> OTHER INFORMATION: R=A or G; Y=C or T

<400> SEQUENCE: 17
gartaycarg agaacggcaa     20

<210> SEQ ID NO 18
<211> LENGTH: 21
<212> TYPE: DNA
<213> ORGANISM: Bacillus stearothermophilus

<400> SEQUENCE: 18
ttcaatgcaa ttactattct t     21

<210> SEQ ID NO 19
<211> LENGTH: 54
<212> TYPE: DNA
<213> ORGANISM: Bacillus stearothermophilus

<400> SEQUENCE: 19
gtgggatccg catgcggagg taaaaaaatg ataaaagtgg catcattatt ttct     54

<210> SEQ ID NO 20
<211> LENGTH: 48
<212> TYPE: DNA
<213> ORGANISM: Bacillus stearothermophilus

<400> SEQUENCE: 20
gtgggatccg catgcttatt tgatttcaag aagttgctta tttgtttt     48

<210> SEQ ID NO 21
<211> LENGTH: 20
<212> TYPE: DNA
<213> ORGANISM: Bacillus stearothermophilus
<220> FEATURE:
<223> OTHER INFORMATION: N=G,A,C or T; R=A or G

<400> SEQUENCE: 21
atgatgacng arttraaraa     20

<210> SEQ ID NO 22
<211> LENGTH: 33
<212> TYPE: DNA
<213> ORGANISM: Bacillus stearothermophilus -continued

```
<400> SEQUENCE: 22
tgtggatcct cctgtataat accaagaggc tta                                33

<210> SEQ ID NO 23
<211> LENGTH: 24
<212> TYPE: DNA
<213> ORGANISM: Bacillus stearothermophilus

<400> SEQUENCE: 23
aagttcgatt aatgcgttaa atgg                                          24

<210> SEQ ID NO 24
<211> LENGTH: 24
<212> TYPE: DNA
<213> ORGANISM: Bacillus stearothermophilus

<400> SEQUENCE: 24
tatgataatc agattccaac agga                                          24

<210> SEQ ID NO 25
<211> LENGTH: 20
<212> TYPE: DNA
<213> ORGANISM: Bacillus stearothermophilus
<220> FEATURE:
<223> OTHER INFORMATION: R=A or G; N=G,A,C or T

<400> SEQUENCE: 25
atgatgacng arttraaraa                                               20

<210> SEQ ID NO 26
<211> LENGTH: 20
<212> TYPE: DNA
<213> ORGANISM: Bacillus stearothermophilus
<220> FEATURE:
<223> OTHER INFORMATION: N=G,A,C or T; R=A or G

<400> SEQUENCE: 26
atgatgacng arctnaaraa                                               20

<210> SEQ ID NO 27
<211> LENGTH: 20
<212> TYPE: DNA
<213> ORGANISM: Bacillus stearothermophilus

<400> SEQUENCE: 27
atgatgaccg aacttaaaaa                                               20

<210> SEQ ID NO 28
<211> LENGTH: 7
<212> TYPE: PRT
<213> ORGANISM: Bacillus stearothermophilus

<400> SEQUENCE: 28

Met Met Thr Glu Leu Lys Asn
 1               5

<210> SEQ ID NO 29
<211> LENGTH: 54
<212> TYPE: DNA
<213> ORGANISM: Bacillus stearothermophilus

<400> SEQUENCE: 29
ggaggagtcc atatgatgac cgaactgaaa aactccaact gcattgaaga gtat         54
```

-continued

```
<210> SEQ ID NO 30
<211> LENGTH: 45
<212> TYPE: DNA
<213> ORGANISM: Bacillus stearothermophilus

<400> SEQUENCE: 30
ggaggatcct tattttttta taatttgatc caacattttg tcaat            45
```